United States Patent
Liu et al.

(10) Patent No.: US 11,952,468 B2
(45) Date of Patent: Apr. 9, 2024

(54) METABOLIC ENZYME-INDUCED MICRO-NANO PLASTIC PARTICLE BIODEGRADATION METHOD AND PRODUCT ANALYSIS METHOD THEREFOR

(71) Applicant: RESEARCH CENTER FOR ECO-ENVIRONMENTAL SCIENCES, CHINESE ACADEMY OF SCIENCES, Beijing (CN)

(72) Inventors: Qian Liu, Beijing (CN); Xiu Huang, Beijing (CN); Guibin Jiang, Beijing (CN)

(73) Assignee: RESEARCH CENTER FOR ECO-ENVIRONMENTAL SCIENCES, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 18/274,244

(22) PCT Filed: Nov. 4, 2021

(86) PCT No.: PCT/CN2021/128825
§ 371 (c)(1),
(2) Date: Jul. 26, 2023

(87) PCT Pub. No.: WO2022/160841
PCT Pub. Date: Aug. 4, 2022

(65) Prior Publication Data
US 2024/0043650 A1    Feb. 8, 2024

(30) Foreign Application Priority Data
Jan. 27, 2021  (CN) .......................... 202110114200.X (51) Int. Cl.
*C08J 11/10*   (2006.01)
*C08J 3/12*    (2006.01)
(Continued)

(52) U.S. Cl.
CPC ............... *C08J 11/105* (2013.01); *C08J 3/12* (2013.01); *C12N 9/1088* (2013.01);
(Continued)

(58) Field of Classification Search
CPC ................. G01N 27/623; G01N 1/4022; C08J 11/105; C08J 3/203; C08J 3/226
See application file for complete search history.

(56) References Cited

U.S. PATENT DOCUMENTS

2014/0275436 A1    9/2014  Huang
2019/0345472 A1*  11/2019  Marty .................... C12N 15/74

FOREIGN PATENT DOCUMENTS

| CN | 103170089 A | 6/2013 |
| CN | 109900774 A | 6/2019 |
| CN | 112903805 A | 6/2021 |

OTHER PUBLICATIONS

Dayyabu Shehu, et al., Dechlorination of polychlorobiphenyl degradation metabolites by a recombinant glutathione S-transferase from *Acidovorax* sp. KKS102, FEBS Open Bio, 2019, pp. 408-419, vol. 9.

(Continued)

*Primary Examiner* — David E Smith
*Assistant Examiner* — Hsien C Tsai
(74) *Attorney, Agent, or Firm* — Bayramoglu Law Offices LLC (57) ABSTRACT

A metabolic enzyme-induced micro-nano plastic particle biodegradation method and a product analysis method therefor are disclosed. The biodegradation method includes the following steps: step (1), cutting an appropriate quantity of plastic products into small pieces; step (2), placing the plastic products in a ball mill tank and milling the plastic products in vacuum in a ball mill; step (3), weighing and dispersing the milled plastic sample with water to prepare a (Continued)

dispersion with a concentration; step (4), mixing the micro-nano plastic dispersion with a metabolic enzyme solution, and placing the mixed solution in a vortex oscillator for mixing well; and step (5), incubating the mixed solution in a waterproof incubator. The present invention provides for the first time a method for biodegradation and metabolism of micro-nano plastics under mild conditions and under the induction of a metabolic enzyme, namely, glutathione S-transferase.

20 Claims, 6 Drawing Sheets

(51) Int. Cl.
*C12N 9/10* (2006.01)
*G01N 1/40* (2006.01)
*G01N 27/623* (2021.01)

(52) U.S. Cl.
CPC ......... *G01N 1/4022* (2013.01); *G01N 27/623* (2021.01); *C08J 2400/20* (2013.01); *G01N 2001/4027* (2013.01)

(56) References Cited

OTHER PUBLICATIONS

Nadia A. Samak, et al., Recent advances in biocatalysts engineering for polyethylene terephthalate plastic waste green recycling, Environment International, 2020, pp. 1-18, vol. 145, 106144.

Luo Wei, Progress on Co-metabolism of Biorefractory Pollutants, Chinese Journal of Soil Science, 2012, pp. 1515-1521, vol. 43, No. 6.

* cited by examiner

METABOLIC ENZYME-INDUCED MICRO-NANO PLASTIC PARTICLE BIODEGRADATION METHOD AND PRODUCT ANALYSIS METHOD THEREFOR

CROSS REFERENCE TO THE RELATED APPLICATIONS

This application is the national phase entry of International Application No. PCT/CN2021/128825, filed on Nov. 4, 2021, which is based upon and claims priority to Chinese Patent Application No. 202110114200.X, filed on Jan. 27, 2021, the entire contents of which are incorporated herein by reference.

TECHNICAL FIELD

The present invention belongs to the field of biodegradation and analysis therefor, and more specifically relates to a metabolic enzyme-induced micro-nano plastic biodegradation method and a product analysis method therefor.

BACKGROUND

Plastic waste has caused many environmental problems. About 359 million tons of plastics are produced globally every year, of which 150 to 200 million tons are quickly turned into waste and directly exposed to nature. Bulk plastics may degrade into micro-scale or nano-scale fragments upon exposure to solar radiation, mechanical force, and microbial action. Micro-nano plastics are considered as an emerging environmental pollutant and widely exist in the natural environment. Micro plastics refer to plastic fragments, particles, fibers or foam with a particle size of 5 mm, and plastics with a particle size of less than 1 μm are referred to as nano plastics. A lot of non-degradable small plastic fragments have been discharged into the environment. Micro plastics in the ocean are even regarded as "PM2.5 in the ocean", and will eventually enter the food chain and ecosystem with the ingestion of marine organisms. Micro/nano plastics may accumulate in organisms to threaten marine ecosystems and human health. In addition, micro-nano plastics have also been found in terrestrial ecosystems. Researches show that micro-nano plastics may also accumulate in soil and occur in organisms such as earthworms and chickens.

Mass accumulated micro-nano plastics may cause adverse biological effects. Bioaccumulation and amplification effects enable micro-nano plastics to accumulate in organisms of different trophic levels, resulting in serious impacts on the entire food web. Previous researches have shown that the ingestion of micro-nano plastics by organisms may cause many effects, including reduction of ingestion activities and depletion of energy reserves, and even individual death. The accumulation of micro-nano plastics in the body may also cause strong inflammatory reactions. However, other adverse health effects related to the micro-nano plastics, such as mortality and incidence rate, are still unclear. Therefore, researches on the occurrence, distribution, and metabolic processes of micro-nano plastics in organisms are of great significance for evaluating the safety of micro-nano plastics and tracing their fate. Before this, most of the plastics are normally considered to be relatively chemically inert, resistant to degradation, particularly in human body.

To accurately monitor the fate of micro-nano plastics in organisms, researchers have been trying to offer available and standardized analytical methods to identify and quantify micro-nano plastics in complex media. Based on the polymer properties and high molecular weights of micro-nano plastics, MALDI-TOF MS with soft ionization and wide mass range provides an effective tool for their characterization. In this research, we used MALDI-TOF MS to monitor the degradation process of micro-nano plastics and investigated the degradation mechanism.

SUMMARY

The present invention aims to provide a very common method for efficiently degrading micro-nano plastic particles under mild conditions by metabolic enzymes, in response to the problems that micro-nano plastics are currently considered to have inert chemical properties and be extremely non-biodegradable. The present application confirms that metabolic enzymes may induce the degradation of micro-nano plastics through many characterizations, especially mass spectrometry characterization, and further elaborates the pathways of biodegradation of micro-nano plastics.

To achieve the above objectives, the present invention provides the following technical solution:

A metabolic enzyme-induced micro-nano plastic particle biodegradation method includes the following steps:
    step (1), cutting an appropriate quantity of plastic products into small pieces;
    step (2), placing the plastic products in a ball mill tank and milling the plastic products in vacuum in a ball mill;
    step (3), weighing and dispersing the milled plastic sample with water to prepare a dispersion with a concentration;
    step (4), mixing the micro-nano plastic dispersion with a metabolic enzyme solution in a mass ratio range of a metabolic enzyme mixed with micro-nano plastics of 0.00000001-10000, and placing the mixed solution in a vortex oscillator for mixing well, where the metabolic enzyme includes glutathione S-transferase; and
    step (5), incubating the mixed solution in a waterproof incubator.

Further, the plastics are milled in the ball mill for 6 h-24 h.

Further, the micro-nano plastics in step (4) may be obtained by flotation of the milled plastic products, and the flotation process requires the addition of a surfactant and mechanical stirring.

Further, the incubation time is set to 0-14 days, and a concentration range of the micro-nano plastic dispersion is 0.0000001 μg/mL-1000 μg/mL.

Further, the glutathione S-transferase in step (4) comes from animals or plants.

Further, the incubation environment in step (5) is a dark or light environment, with a temperature range of 15° C.-37° C.

On the other hand, a product analysis method for the metabolic enzyme-induced micro-nano plastic particle biodegradation method described above includes:
    step (6), adding the mixed solution incubated for a period of time onto an MTP 384 stainless steel unpolished target plate dropwise;
    step (7), placing the target plate in a fume cupboard without adding any matrix, and evaporating the sample naturally; and
    step (8), after the sample is dried, placing the target plate on a target holder of MALDI-TOF MS, and directly performing mass spectrometry test on the micro-nano plastic sample through the MALDI-TOF MS.

Further, a mass spectrum range of characteristic absorption and degradation products of micro-nano plastic particles obtained in step (8) is 0-2000 m/z.

Further, the mass spectrum range of characteristic absorption and degradation products of the micro-nano plastic particles obtained in step (8) is in small molecule regions of less than 1000 m/z. Further, degradation pathways for the micro-nano plastic particles obtained in step (8) include an oxidation pathway and a nitridation pathway.

Further, actual to-be-tested samples in step (8) may be plastic products from environmental or biological samples, and characterization technologies include morphological characterization and mass spectrometry molecular characterization.

The metabolic enzyme-induced micro-nano plastic particle biodegradation method and the product analysis method therefor, provided in the present invention, have the following beneficial effects:

9. The present invention discovers that the ball milling process may change surface properties of micro-nano plastics, thereby promoting their degradation.
10. The present invention provides a new enzymatic method for removing micro-nano plastic pollution based on the special degradation ability of metabolic enzymes on micro-nano plastics.
11. The present invention found that the micro-nano plastics may be metabolized and transformed by metabolic enzymes under mild conditions. Multiple degradation products were identified through mass spectrometry. These findings update our past understanding of the biological fate of micro-nano plastics.
12. The present invention can implement high-sensitive mass spectrometry test without adding any matrix during sample preparation, thereby simplifying operation steps, saving sample preparation time, and greatly improving test efficiency.
13. In the absence of any additional matrix, the present invention reduces a co-crystallization process, overcomes common hot spot problems in conventional matrices, improves analysis reproducibility, and reduces costs.
14. The present invention implements rapid and high-throughput mass spectrometry test of complex environmental samples.
15. The matrix-free test method based on a dual ion mode of matrix assisted laser desorption ionization time of flight mass spectrometry requires a little sample with a small volume, and can implement high-sensitive mass spectrometry test of micro-nano plastics, with a test limit of up to or even lower than the ppt level.
16. The matrix-free test method based on a dual ion mode of matrix assisted laser desorption ionization time of flight mass spectrometry has the characteristics of quickness, high efficiency, high sensitivity, stable signals, high throughput, and high accuracy, and has the possibility of quantifying micro-nano plastics.

BRIEF DESCRIPTION OF THE DRAWINGS

To describe the technical solutions in the embodiments of the present invention or in the prior art more clearly, the following briefly introduces the accompanying drawings required for describing the embodiments or the prior art. Apparently, the drawings in the following description show some embodiments of the present invention, and those of ordinary skill in the art may still derive other drawings from these drawings without any creative efforts.

FIG. 2 show optical photos of micro-nano plastics incubated with glutathione S-transferase at different time using a metabolic enzyme-induced micro-nano plastic particle biodegradation method and a product analysis method therefor according to an embodiment of the present invention, where the incubation time of FIGS. 2A-2C is 0 h, 12 h, and 96 h, respectively.

DETAILED DESCRIPTION OF THE EMBODIMENTS

To make the objectives, technical solutions, and advantages of the embodiments of the present invention clearer, the following clearly and completely describes the technical solutions in the embodiments of the present invention with reference to the accompanying drawings in the embodiments of the present invention. Apparently, the described embodiments are some but not all of the embodiments of the present invention. All other embodiments obtained by those of ordinary skill in the art based on the embodiments of the present invention without any creative efforts shall fall within the protection scope of the present invention.

The inventor of the present application found in the research that:

(1) Micro-nano plastics have characteristic molecular peaks in low mass regions in MALDI-TOF MS, where the characteristic peaks of monomers and degradation products of the micro-nano plastics are 0-2000, especially in small molecule regions less than 1000.
(2) Under mild conditions, micro-nano plastics may be metabolized and transformed by metabolic enzymes.
(3) A ball milling process may change surface properties of micro-nano plastics, thereby promoting their degradation.

Therefore, the present invention provides a metabolic enzyme-induced micro-nano plastic particle biodegradation method, including the following steps:

step (1), cutting an appropriate quantity of plastic products into small pieces;

step (2), placing the plastic products in a ball mill tank and milling the plastic products in vacuum in a ball mill;

step (3), weighing and dispersing the milled plastic sample with water to prepare a dispersion with a concentration;

step (4): mixing the micro-nano plastic dispersion with a metabolic enzyme solution, and placing the mixed solution in a vortex oscillator for mixing well; and step (5), incubating the mixed solution in a waterproof incubator.

On the other hand, the present application further provides a product analysis method for the metabolic enzyme-induced micro-nano plastic particle biodegradation method, including:

step (6), adding the mixed solution incubated for a period of time onto an MTP 384 stainless steel non-polished target plate dropwise;

step (7), placing the target plate in a fume cupboard without adding any matrix, and evaporating the sample naturally; and step (8), after the sample is dried, placing the target plate on a target holder of MALDI-TOF MS, and directly performing mass spectrometry test on the micro-nano plastic sample through the MALDI-TOF MS.

Further, the inventor of the present application carried out relevant experimental verification:

(1) MALDI-TOF MS test of the analysis method was carried out in a reflection mode, and the analysis method was applicable in both positive and negative ion modes.

(2) When the analysis method was applied in the positive ion mode, laser power of mass spectrometry was set to 15%-90%, a frequency was set to 100-200, and shots were set to 100-500; and in the negative ion mode, laser power of mass spectrometry was set to 15%-90%, a frequency was set to 100-200, and shots were set to 100-500.

(3) A concentration range of the micro-nano plastic dispersion prepared by the analysis method was 0.0000001 µg/mL-1000 µg/mL.

(4) The plastics in the analysis method were milled continuously or intermittently in the ball mill for 6 h-24 h.

(5) The micro-nano plastics in the analysis method may be obtained by flotation of the milled plastic products, and the flotation process required the addition of a surfactant and mechanical stirring.

(6) The incubation time in the analysis method was in the range of 0-14 days, and a mass ratio range of a metabolic enzyme mixed with micro-nano plastics was 0.00000001 to 10000.

(7) The metabolic enzyme in the analysis method was glutathione S-transferase from animals and plants.

(8) The analysis method can implement high-sensitive mass spectrometry test without adding any matrix during sample preparation.

(9) The micro-nano plastics obtained by the analysis method had characteristic monomer cluster peaks in MALDI-TOF MS, with characteristic fingerprint peaks ranging from 0 to 2000 m/z, especially in small molecule regions below 1000 m/z.

(10) The incubation environment in the analysis method was a dark and light environment, with a temperature range of 15° C.-37° C.

(11) The degradation products of micro-nano plastic particles in the analysis method ranged from 0 to 2000 m/z, especially in small molecule regions below 1000 m/z.

(12) Degradation pathways for the micro-nano plastic particles in the analysis method included an oxidation pathway and a nitridation pathway.

(13) Actual to-be-tested samples in the analysis method may be plastic products from environmental or biological samples.

(14) The analysis method may be used to characterize the mixed liquid sample obtained in step (5), such as optical photos and mass spectrometry technology.

(15) The analysis method used small samples in a range of 1 µL-10 µL.

EXAMPLE

Figure 1A:
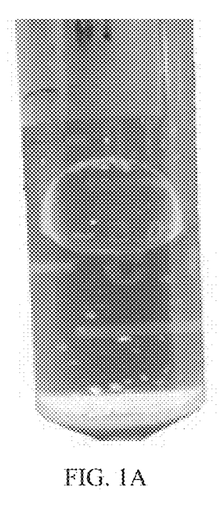
FIGS. 1A-1D show optical photos of micro-nano plastics incubated with glutathione S-transferase at different time using a metabolic enzyme-induced micro-nano plastic particle biodegradation method and a product analysis method therefor according to an embodiment of the present invention, where the incubation time of FIGS. 1A-1D is 0 h, 24 h, 48 h, and 96 h, respectively.
Figure 1B:
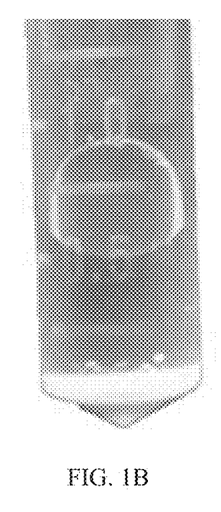
Figure 1C:
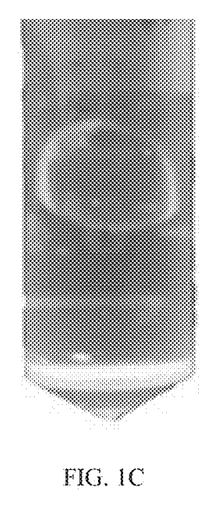
Figure 1D:
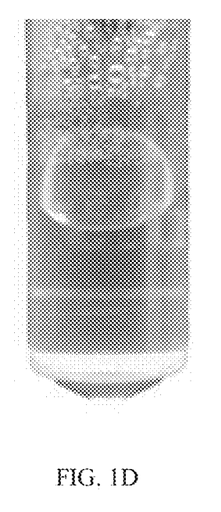
Figure 2A:
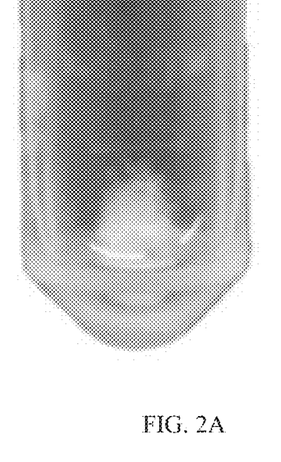
Figure 2B:
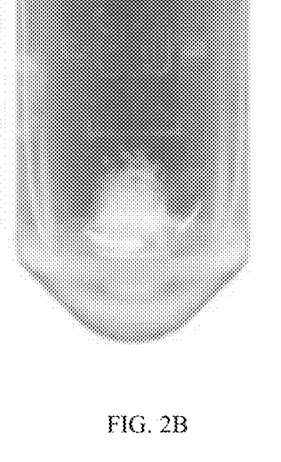
Figure 2C:
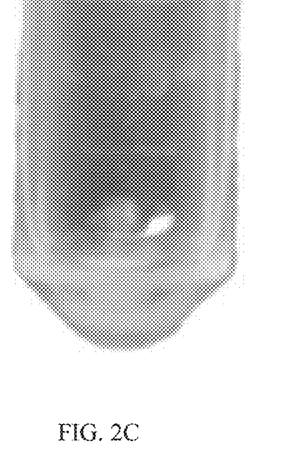
Figure 3:
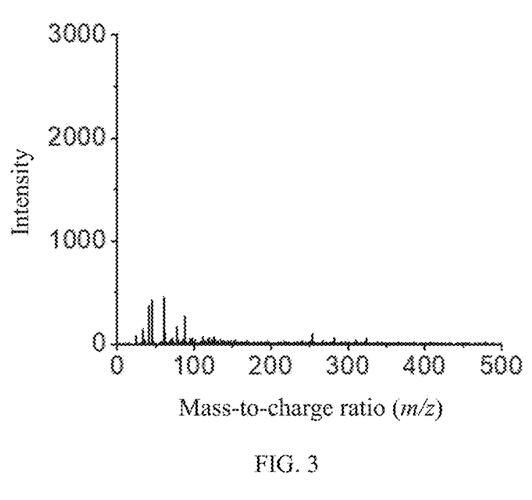
FIG. 3 shows MALDI-TOF MS test results of 1 μL of micro-nano plastics in low mass regions using a metabolic enzyme-induced micro-nano plastic particle biodegradation method and a product analysis method therefor according to an embodiment of the present invention.
Figure 4:
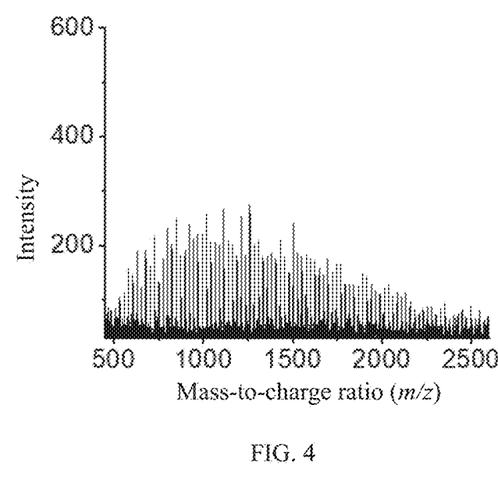
FIG. 4 shows MALDI-TOF MS test results of 1 μL of micro-nano plastics in high mass regions using a metabolic enzyme-induced micro-nano plastic particle biodegradation method and a product analysis method therefor according to an embodiment of the present invention.
Figure 5:
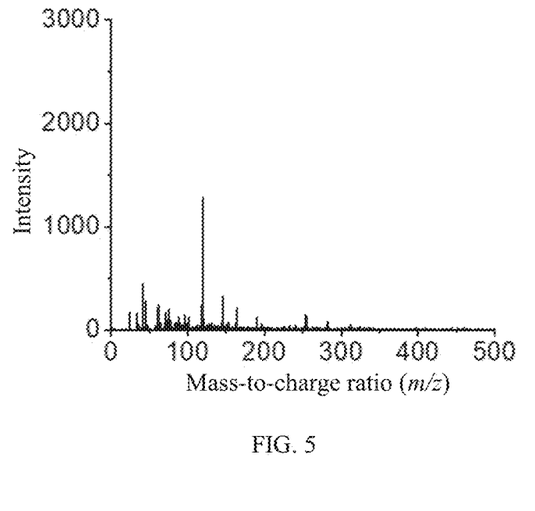
FIG. 5 is a typical MALDI-TOF MS mass spectrogram of 1 μL of micro-nano plastics incubated with glutathione S-transferase for 12 h using a metabolic enzyme-induced micro-nano plastic particle biodegradation method and a product analysis method therefor according to an embodiment of the present invention.
Figure 6:
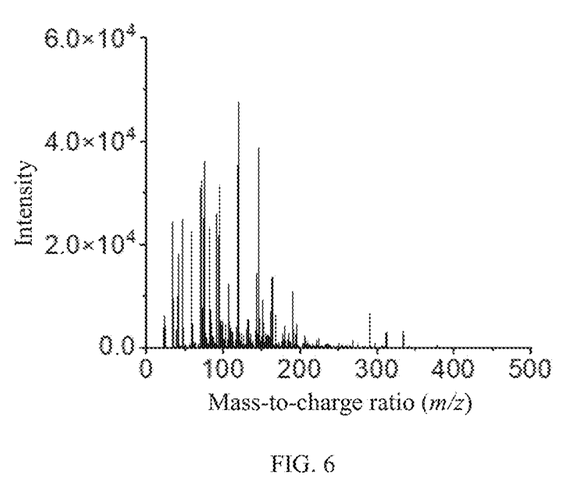
FIG. 6 is a typical MALDI-TOF MS mass spectrogram of 1 μL of micro-nano plastics incubated with glutathione S-transferase for 96 h using a metabolic enzyme-induced micro-nano plastic particle biodegradation method and a product analysis method therefor according to an embodiment of the present invention.

An appropriate quantity of PET plastic products were cut into small pieces, placed in a ball mill tank, and milled in vacuum in a ball mill. The milled plastic sample was dispersed with water to prepare a dispersion with a concentration. Then, the micro-nano plastic dispersion was mixed with a metabolic enzyme solution, and the mixed solution was placed in a vortex oscillator for mixing well and incubated in a waterproof incubator. After incubation for a period of time, 1 µL of the mixed solution was added dropwise with a pipette onto a commercial MTP 384 stainless steel unpolished target plate, the target plate was placed in a fume cupboard without adding any matrix, and the sample was evaporated naturally. After the sample was dried, the target plate was placed on a target holder of MALDI-TOF MS, and mass spectrometry test was directly performed on the micro-nano plastic sample through the MALDI-TOF MS. The used instrument model was Bruker-DaltonicsAutoflex III Stnartbean MALDI-TOF mass spectrometer, which used 355 nm Nd:YAG with a frequency of 200 Hz. In a negative ion mode, laser power was set to 70%, and a mass spectrometry test range was 0-3000. In a positive ion mode, laser power was set to 70% and a mass spectrometry test range was 1-3000. Test results were shown in FIGS. 1-6. FIGS. 1A-1D show optical photos of micro-nano plastics degraded by a metabolic enzyme, showing results of incubation with glutathione S-transferase for 0 h, 24 h, 48 h, and 96 h from FIG. 1A to FIG. 1l), respectively. FIGS. 2A-2C show optical photos of micro-nano plastics degraded by a metabolic enzyme, showing results of incubation with glutathione S-transferase for 0 h, 12 h, and 96 h from FIG. 2A to FIG. 2C, respectively. FIG. 3 shows MALDI-TOF MS test results of micro-nano plastics in low mass regions. FIG. 4 shows MALDI-TOF MS test results of micro-nano plastics in high mass regions. FIG. 5 shows MALDI-TOF MS test results of micro-nano plastics after incubation with glutathione S-transferase in a dark environment at 37° C. for 12 h. FIG. 6 shows MALDI-TOF MS test results of micro-nano plastic samples after incubation with glutathione S-transferase in a dark environment at 37° C. for 96 h. It may be seen from FIGS. 1A-1D and FIGS. 2A-2C that, after the addition of glutathione S-transferase, micro-nano plastics gradually decreased over time, indicating that glutathione S-transferase induced metabolic transformation of the micro-nano plastics. It may be seen from FIG. 3 and FIG. 4 that, in the absence of a matrix, the tested micro-nano plastics had characteristic molecular peak clusters in MALDI-TOFMS no matter in low mass regions or high mass regions, indicating that the analysis method in this example can be directly used for the analysis of micro-nano plastic samples without adding any matrix during sample preparation. It may be seen from FIG. 5 and FIG. 6 that the MALDI-TOF MS further proved that the glutathione transferase induced the metabolic transformation of micro-nano plastics. The transformed products were mainly divided into two classes, namely, oxidation products and nitridation products. These findings show that plastics may be degraded in organisms, even in the human body. The human body has certain ability to clear plastics.

From the above example, the present application found through research that micro-nano plastics may be biodegraded and metabolized under mild conditions and under the induction of a metabolic enzyme, namely, glutathione S-transferase. Plastics are conventionally considered inert and may resist biological digestion or degradation. The present invention found through research that micro-nano plastics may be degraded by glutathione S-transferase under mild conditions, and this process has been demonstrated through multiple complementary technologies. In the present invention, multiple degradation products were discovered through mass spectrometry, and a transformation mechanism of micro-nano plastic particles in organisms was provided accordingly. These findings update understanding of the biological fate of micro-nano plastics in the prior art. A new enzymatic method for removing micro-nano plastic pollution was provided based on the special degradation ability of metabolic enzymes on micro-nano plastics.

The above embodiments are only for explaining, but not limiting, the technical solutions of the present invention. Although the present invention is described in detail with reference to the foregoing embodiments, those of ordinary skill in the art should understood that the technical solutions described in the foregoing embodiments may be modified, or some of the technical features may be equivalently substituted. These modifications or substitutions do not make the essence of the corresponding technical solutions depart from the spirit and scope of the technical solutions of the present invention.

What is claimed is:

1. A metabolic enzyme-induced micro-nano plastic particle biodegradation method, comprising the following steps:
    step (1), cutting an appropriate quantity of plastic products into small pieces;
    step (2), placing the plastic products in a ball mill tank and milling the plastic products in a vacuum in a ball mill;
    step (3), weighing and dispersing milled plastic products with water to prepare a micro-nano plastic dispersion with a concentration;
    step (4), mixing the micro-nano plastic dispersion with a metabolic enzyme solution in a mass ratio range of a metabolic enzyme mixed with micro-nano plastics of 0.00000001-10000, and placing a mixed solution in a vortex oscillator for mixing well, wherein the metabolic enzyme comprises glutathione S-transferase; and
    step (5), incubating the mixed solution in a waterproof incubator.

2. The metabolic enzyme-induced micro-nano plastic particle biodegradation method according to claim 1, wherein the plastics are milled in the ball mill for 6 h-24 h.

3. The metabolic enzyme-induced micro-nano plastic particle biodegradation method according to claim 1, wherein the micro-nano plastics in step (4) are obtained by a flotation process of the milled plastic products, and the flotation process requires an addition of a surfactant and a mechanical stirring.

4. The metabolic enzyme-induced micro-nano plastic particle biodegradation method according to claim 1, wherein an incubation time is set to 0-14 days, and a concentration range of the micro-nano plastic dispersion is 0.0000001 μg/Ml-1000 μg/Ml.

5. The metabolic enzyme-induced micro-nano plastic particle biodegradation method according to claim 1, wherein the glutathione S-transferase in step (4) comes from animals or plants.

6. The metabolic enzyme-induced micro-nano plastic particle biodegradation method according to claim 1, wherein an incubation environment in step (5) is a dark or light environment, with a temperature range of 15° C.-37° C.

7. The metabolic enzyme-induced micro-nano plastic particle biodegradation method according to claim 1, wherein a degradation rate of micro-nano plastic particles incubated in step (5) is 50%-100%.

8. The metabolic enzyme-induced micro-nano plastic particle biodegradation method according to claim 1, wherein a mass spectrum range of a characteristic absorption and degradation products of micro-nano plastic particles incubated in step (5) is 0-2000 m/z.

9. The metabolic enzyme-induced micro-nano plastic particle biodegradation method according to claim 8, wherein the mass spectrum range of the characteristic absorption and the degradation products of the micro-nano plastic particles incubated in step (5) is in small molecule regions of less than 1000 m/z.

10. The metabolic enzyme-induced micro-nano plastic particle biodegradation method according to claim 1, wherein degradation pathways for micro-nano plastic particles incubated in step (5) comprise an oxidation pathway and a nitridation pathway.

11. The metabolic enzyme-induced micro-nano plastic particle biodegradation method according to claim 1, wherein the plastic products in step (1) are plastic products from environmental or biological samples, and characterization technologies comprise a morphological characterization and a mass spectrometry molecular characterization.

12. A product analysis method for the metabolic enzyme-induced micro-nano plastic particle biodegradation method according to claim 1, comprising:
    step (6), adding the mixed solution incubated for a period of time onto an MTP 384 stainless steel non-polished target plate dropwise;
    step (7), placing the MTP 384 stainless steel non-polished target plate in a fume cupboard without adding a matrix, and evaporating a sample naturally; and
    step (8), after the sample is dried, placing the MTP 384 stainless steel non-polished target plate on a target holder of a matrix-assisted laser desorption/ionization time of flight mass spectrometer (MALDI-TOF MS), and directly performing a mass spectrometry test on the sample through the MALDI-TOF MS.

13. The metabolic enzyme-induced micro-nano plastic particle biodegradation method according to claim 2, wherein the micro-nano plastics in step (4) are obtained by a flotation process of the milled plastic products, and the flotation process requires an addition of a surfactant and a mechanical stirring.

14. The metabolic enzyme-induced micro-nano plastic particle biodegradation method according to claim 2, wherein an incubation time is set to 0-14 days, and a concentration range of the micro-nano plastic dispersion is 0.0000001 μg/Ml-1000 μg/Ml.

15. The metabolic enzyme-induced micro-nano plastic particle biodegradation method according to claim 2, wherein the glutathione S-transferase in step (4) comes from animals or plants.

16. The metabolic enzyme-induced micro-nano plastic particle biodegradation method according to claim 2, wherein an incubation environment in step (5) is a dark or light environment, with a temperature range of 15° C.-37° C.

17. The metabolic enzyme-induced micro-nano plastic particle biodegradation method according to claim 2, wherein a degradation rate of micro-nano plastic particles incubated in step (5) is 50%-100%.

18. The metabolic enzyme-induced micro-nano plastic particle biodegradation method according to claim 2, wherein a mass spectrum range of a characteristic absorption and degradation products of micro-nano plastic particles incubated in step (5) is 0-2000 m/z.

19. The metabolic enzyme-induced micro-nano plastic particle biodegradation method according to claim 2, wherein degradation pathways for micro-nano plastic particles incubated in step (5) comprise an oxidation pathway and a nitridation pathway.

20. The metabolic enzyme-induced micro-nano plastic particle biodegradation method according to claim 3, wherein degradation pathways for micro-nano plastic particles incubated in step (5) comprise an oxidation pathway and a nitridation pathway.

* * * * *